(12) United States Patent
Losell

(10) Patent No.: US 7,632,474 B2
(45) Date of Patent: Dec. 15, 2009

(54) DEVICE, CARTRIDGE AND METHOD FOR SOLVING POWDER IN LIQUID, WHEN MANUFACTURING A DIALYSIS FLUID

(75) Inventor: Ernst Ingvar Losell, Staffanstorp (SE)

(73) Assignee: Gambro Lundia AB (SE)

( * ) Notice: Subject to any disclaimer, the term of this patent is extended or adjusted under 35 U.S.C. 154(b) by 820 days.

(21) Appl. No.: 10/552,604

(22) PCT Filed: Mar. 23, 2004

(86) PCT No.: PCT/SE2004/000436

§ 371 (c)(1),
(2), (4) Date: Oct. 5, 2005

(87) PCT Pub. No.: WO2004/089441

PCT Pub. Date: Oct. 21, 2004

(65) Prior Publication Data

US 2006/0292048 A1 Dec. 28, 2006

Related U.S. Application Data

(60) Provisional application No. 60/461,657, filed on Apr. 7, 2003.

(30) Foreign Application Priority Data

Apr. 7, 2003 (SE) .................................. 0301044

(51) Int. Cl.
*B01D 11/02* (2006.01)
*B01D 35/00* (2006.01)
*B01D 24/00* (2006.01)
*A61L 2/00* (2006.01)
*C02F 1/76* (2006.01)
*B67D 5/56* (2006.01)
*B67D 5/58* (2006.01)
*A61M 1/00* (2006.01)

(52) U.S. Cl. .............................. 422/255; 422/1; 422/28; 422/261; 422/266; 422/270; 422/276; 422/277; 422/292; 422/302; 422/901; 422/902; 210/749; 210/753; 210/206; 210/295; 210/321.6; 210/323.1; 210/348; 222/129; 222/189.06; 222/190; 604/29

(58) Field of Classification Search ..................... 422/1, 422/28, 255, 261, 266, 270, 276, 277, 292, 422/302, 901, 902; 210/749, 753, 206, 295, 210/321.6, 323.1, 348; 222/129, 189.06, 222/190; 604/29
See application file for complete search history.

(56) References Cited

U.S. PATENT DOCUMENTS 1,932,117 A 10/1933 O'Brien (Continued)

FOREIGN PATENT DOCUMENTS

DE 198 01 107 A1 7/1999

(Continued)

*Primary Examiner*—Jill Warden
*Assistant Examiner*—Monzer R. Chorbaji
(74) *Attorney, Agent, or Firm*—Finnegan, Henderson, Farabow, Garrett & Dunner L.L.P.

(57) ABSTRACT

The invention provides a device for use in a cartridge for on-line preparation of a solution for a medical procedure. The device comprises a hollow body, the body having a first end and a second end and is provided with through holes in its wall. The second end is closed, while the first end is open and adapted for receiving fluid introduced into the cartridge. The fluid leaves the device through said holes. Furthermore, the invention relates to a cartridge provided with such a device, a method of manufacturing such a cartridge and the use of a charge of concentrate in such a cartridge.

9 Claims, 4 Drawing Sheets

U.S. PATENT DOCUMENTS

| | | | |
|---|---|---|---|
| 2,743,230 A | | 4/1956 | Meyer |
| 2,771,346 A | * | 11/1956 | Lambers .................... 422/278 |
| 2,847,126 A | | 8/1958 | Goodman |
| 3,155,612 A | | 11/1964 | Weber |
| 3,209,915 A | | 10/1965 | Gutkowski |
| 3,317,044 A | | 5/1967 | Marks |
| 3,429,444 A | * | 2/1969 | Robandt et al. ............. 210/356 |
| 3,730,348 A | | 5/1973 | Weis et al. |
| 4,421,646 A | | 12/1983 | Correge et al. |
| 4,734,198 A | | 3/1988 | Harm et al. |
| 4,787,987 A | | 11/1988 | Hensley |
| 4,885,083 A | | 12/1989 | Banks |
| 4,948,505 A | * | 8/1990 | Petrucci et al. ............. 210/238 |
| 5,290,445 A | * | 3/1994 | Buttery ...................... 210/445 |
| 5,356,593 A | | 10/1994 | Heilberger et al. |
| 5,566,611 A | | 10/1996 | Scheucher et al. |
| 5,616,305 A | | 4/1997 | Mathieu |
| 5,637,214 A | | 6/1997 | Kahana |
| 5,707,536 A | | 1/1998 | Meissner |
| 5,976,370 A | | 11/1999 | Medworth |
| 6,296,762 B1 | | 10/2001 | Jönsson et al. |
| 6,444,174 B1 | | 9/2002 | Lascombes |
| 6,776,907 B2 | | 8/2004 | Barlow |
| 2006/0186035 A1 | | 8/2006 | Tryggvason et al. |
| 2006/0292048 A1 | | 12/2006 | Losell |

FOREIGN PATENT DOCUMENTS

| | | |
|---|---|---|
| DE | 20008860 | 9/2000 |
| EP | 0 278 100 B1 | 8/1988 |
| EP | 0439793 | 8/1991 |
| SE | B-467142 | 8/1988 |
| WO | WO 97/29796 | 8/1988 |
| WO | WO 02/087670 | 11/2002 |
| WO | WO 03/059241 | 7/2003 |

* cited by examiner (Prior art) Fig. 1

DEVICE, CARTRIDGE AND METHOD FOR SOLVING POWDER IN LIQUID, WHEN MANUFACTURING A DIALYSIS FLUID

This application is a national stage application under 35 U.S.C. § 371 of International Application No. PCT/SE2004/000436, filed on Mar. 23, 2004, which claims priority from Swedish Application No. 0301044-4, filed on Apr. 7, 2003, and the benefit of U.S. Provisional Application No. 60/461,657, filed on Apr. 7, 2003.

TECHNICAL FIELD OF THE INVENTION

The present invention relates to on-line preparation of a solution intended for a medical procedure, in particular of sodium chloride or bicarbonate solution for hemodialysis. The on-line preparation in view takes place in a cartridge containing a powdered or granular concentrate, such as sodium chloride or sodium bicarbonate. More particular, the invention relates to a device for use in a cartridge of the above-mentioned type, a cartridge provided with such a device, a method of manufacturing such a cartridge and the use of a charge of concentrate in such a cartridge.

To those skilled in the art, it will be apparent that the present invention can be used in connection with other medical procedures where a fluid suitable for the procedure is obtained from mixing of a solvent (e.g. water) with at least one concentrate in powder form, such as replacement fluids in connection with hemodiafiltration and hemofiltration operations.

BACKGROUND OF THE INVENTION

Dialysis is a well-known method for treatment of kidney insufficiency. In hemodialysis, the blood of a patient suffering from impaired kidney function is conducted from a patient blood vessel to a dialysis machine and is returned to the patient after the treatment. The blood is conducted along one side of a permeable membrane in a dialyzer or filter connected to the dialysis machine, at the same time as dialysis fluid or dialysate may be conducted along the opposite side of the same membrane. Waste substances or poisons that are to be removed from the blood pass potentially with the help of diffusion from the blood to the dialysis fluid through the membrane. Excess water is also removed from the blood. A hemodialysis treatment typically lasts 3-5 hours. Preferably, a treatment may be performed while the patient is sleeping during night and may in that case last for about 8 hours.

On-line preparation of dialysis fluid is known. For example, the on-line preparation of a saturated bicarbonate solution from powdered bicarbonate contained in a cartridge is disclosed in DE 198 01 107 A1.

For the preparation of a dialysis fluid, saturated sodium bicarbonate solution may be mixed with a solution comprising appropriate electrolytes, such as $K^+$, $Ca^{2+}$ and $Mg^{2+}$.

In EP 0 278 100 B1 a powder cartridge is shown. The cartridge comprises a closed vessel provided with penetrable membranes at its upper inlet end and its lower outlet end, respectively. Within the vessel, there is provided a supply of powder concentrate of sufficient quantity so as to be suitable for a dialysis treatment session. For instance, in connection with the preparation of dialysis fluid or solution, the concentrate may consist of powdered sodium chloride or sodium bicarbonate.

In use, a powder containing prior-art cartridge is first primed with fluid, such as water, either from the top or from the bottom. Enough fluid is introduced into the cartridge during priming so that the fluid level is above the powder level. The powder is dissolved in the fluid and a saturated solution can leave the cartridge through the outlet in the bottom of the cartridge. As the solution leaves the cartridge a corresponding amount of new fluid is introduced into the cartridge. To establish that the degree of saturation of the solution leaving the cartridge is satisfactory, the conductivity of the solution may be measured. An unsatisfactory conductivity (saturation) will trigger an alarm in the dialysis machine.

The above-mentioned way of on-line preparation of solutions for medical use by means of a powder cartridge has many advantages. There are, however, some disadvantages with prior-art cartridges. After a few hours of use, the mixture of the fluid and the powder in the cartridge may become inhomogeneous. In some instances, clods may be formed. The clods may prevent gas bubbles from rising to the liquid surface. When a bubble is "released", a channel in the powder bed may be created, sometimes all the way down to the lower outlet of the cartridge. This may allow unsaturated solution to leave the cartridge causing a conductivity alarm. The alarm must be taken care of either by the patient or by a nurse or medical attendant. If these problems occur, they may be remedied by knocking on the cartridge wall or by shaking the cartridge. However, often the cartridge has to be discarded, while still containing a considerable amount of powder, and replaced by a new cartridge.

The formation of channels in the powder bed might have other causes. For example, the fluid may be introduced gradually through the top inlet and fall in drops down to and impact the liquid surface. This may give rise to pressure waves in the liquid bed which in turn create fluid currents perpendicular to the powder bed surface. These currents may work their way down in the powder bed, creating channels in the bed reaching the lower outlet, making it possible for unsaturated solution to leave the cartridge.

SUMMARY OF THE INVENTION

In these circumstances it is an object of the present invention to create opportunities for improved on-line preparation of a solution intended for a medical procedure, in particular of sodium chloride or bicarbonate solution for hemodialysis, by means of a powder or granular cartridge. This and other objects are achieved by a device for use in a cartridge, the device comprising the features of the enclosed independent device claim, a cartridge provided with such a device according to the enclosed independent cartridge claim, a method of manufacturing such a cartridge comprising the steps of the enclosed independent method claim, and/or a method of use comprising the features of the enclosed independent use claim. Preferred embodiments are set forth in the enclosed dependent claims and in the following description.

By arranging a device according to the invention in a powder cartridge for online preparation of a solution, the fluid continuously introduced in the cartridge may be distributed in a desired way so as to minimize the risk of formation of channels and inhomogeneities in the powder bed. In turn this minimizes the risk of unsaturated solution leaving the cartridge. Thus, the chance that the whole amount of powder in the cartridge can be used is increased. This is of course favorable, both as regards operating results and costs.

Furthermore, during the initial priming of a cartridge, the inventive device provides a more even distribution of the fluid.

By preferably letting the device being elongated and having the through holes vertically distributed over its elongated wall, it is possible to let the fluid be output below the liquid/air surface also when the liquid level is sinking gradually. Therefore, the fluid does not fall in drops down on the liquid surface. The generation of pressure waves is avoided. Consequently, the formation of channels in the powder bed is minimized.

The device is preferably conical, which means that it easily can be stuck into the dry powder bed when preparing a cartridge.

The inventive cartridge exhibits advantages corresponding to those mentioned above as regards the inventive device.

The manufacturing method according to the invention is simple and cost-effective.

The use of an inventive cartridge, wherein the solvent is entering the vessel via an inventive device, allows a more efficient use of the powder or granulate and longer periods without operating interruptions. This implies a cost-effective process.

DETAILED DESCRIPTION OF PREFERRED EMBODIMENTS

In hemodialysis, the blood of a patient suffering from impaired kidney function is conducted from a patient blood-vessel (of for example the patient forearm) to a dialysis machine and is returned to the patient after the treatment. The blood is conducted along one side of a permeable membrane in a dialyser or filter working with and/or as a part of the dialysis machine. At the same time, a dialysis fluid may be conducted along the opposite side of the same membrane. A transfer of waste substances or poisons and excess water that are to be removed from the blood may take place by the help of diffusion through the membrane from the blood to the dialysis fluid. One dialysis treatment may typically last from about 3 to 8 about hours.

Figure 1:
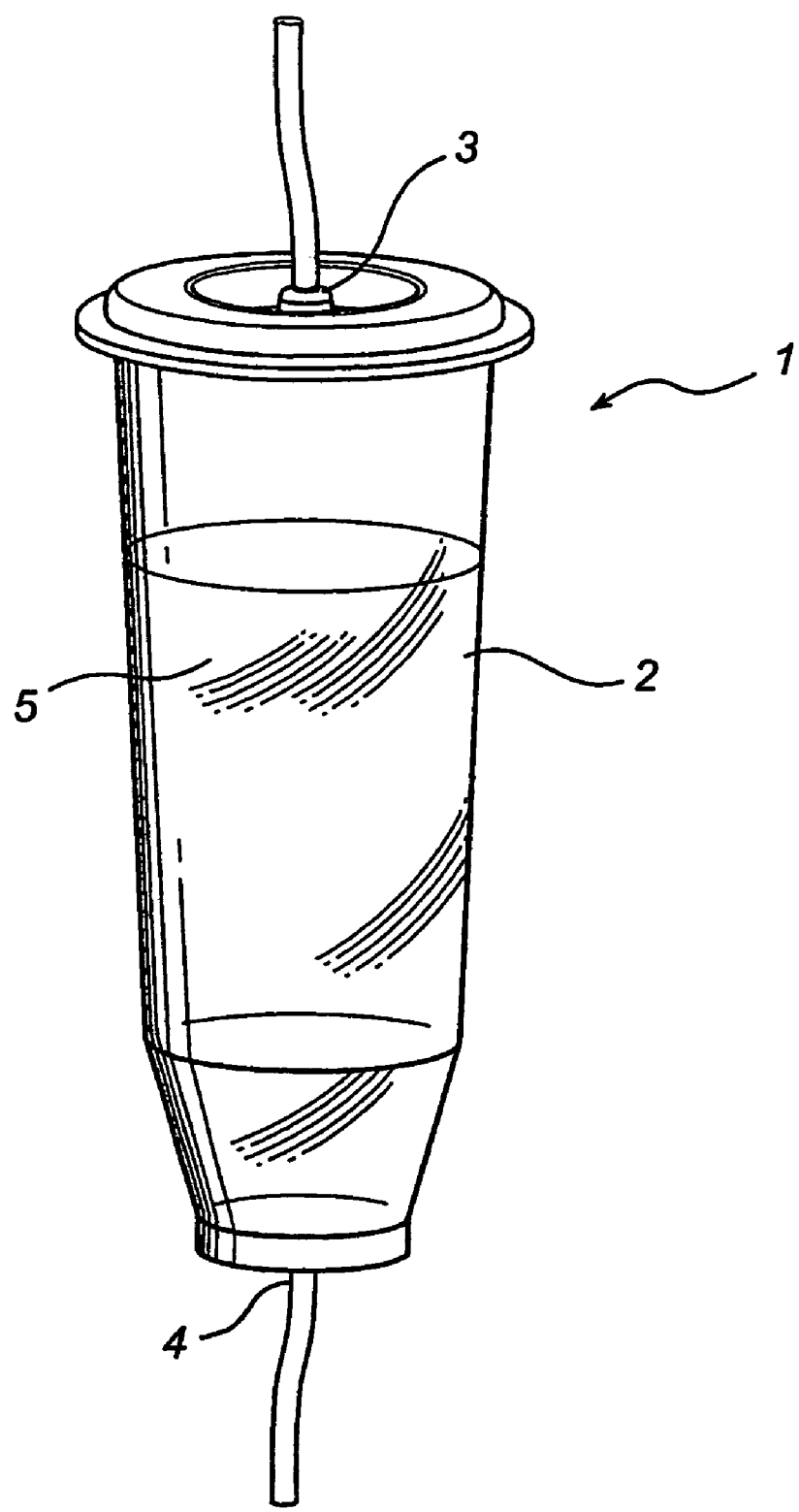
FIG. 1 shows a prior-art cartridge for on-line preparation of a solution.

In FIG. 1, a prior-art cartridge 1 for on-line preparation of a saturated bicarbonate solution from powdered sodium bicarbonate is shown. For the preparation of a dialysis fluid, the saturated sodium bicarbonate solution may be mixed with a solution comprising appropriate electrolytes, such as $K^+$, $Ca^{2+}$ and $Mg^{2+}$. The cartridge 1 may include a closed vessel or container 2 with an upper inlet end 3 and a lower outlet end 4. Within the vessel 2, there is provided a supply of powder concentrate 5 of sufficient quantity so as to be suitable for one or more treatments. The quantity of the powder contained in the cartridge would be on the order of magnitude of 400-1500 grams. Sodium chloride is another typical example in dialysis procedures.

Hereinafter a preferred embodiment of the inventive device for use in a powder or granulate cartridge will be described.

Figure 2:
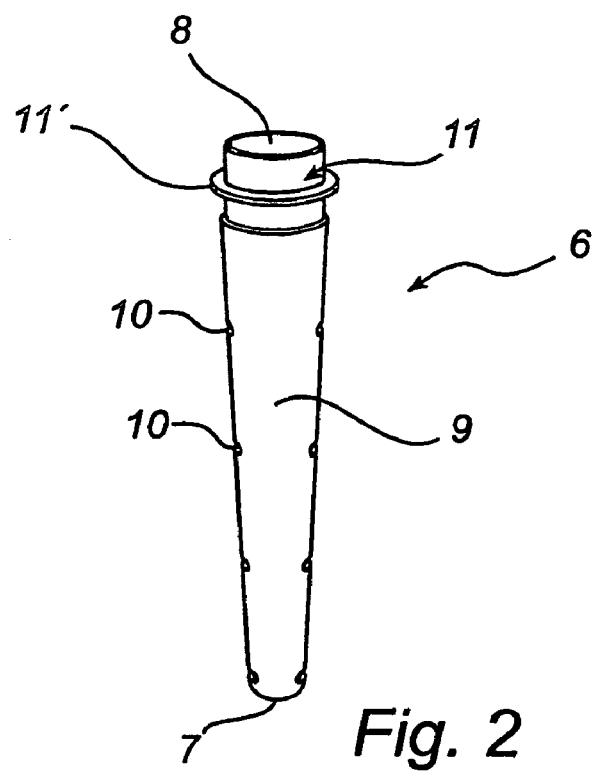
FIG. 2 shows a device according to a preferred embodiment of the invention for use in a cartridge.
Figure 3:
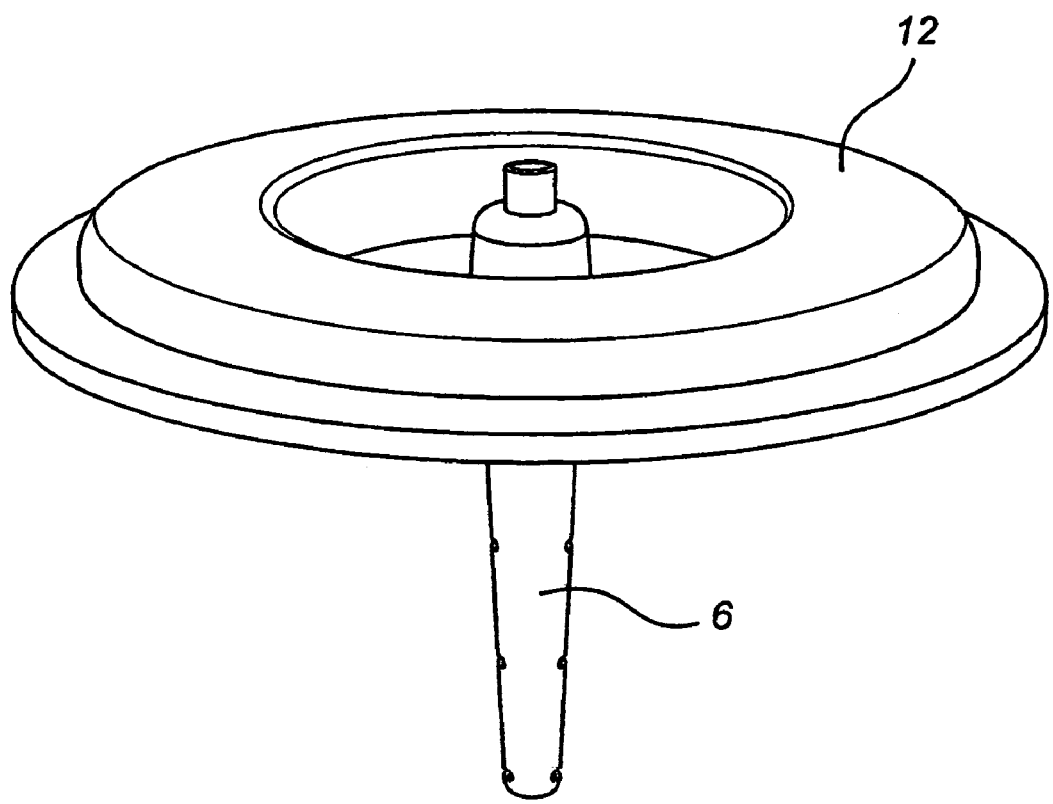
FIG. 3 shows an inventive device attached to a cartridge lid.

A device 6 according to the invention is shown in FIG. 2. The device comprises an elongated, and in some embodiments substantially conical tube 6 made typically of a plastic such as polypropylene. The tube 6 isclosed at its lower end 7 and open at its upper end 8. In the wall 9 of the tube 6 through holes 10 are provided. This particular embodiment has eight holes 10 arranged in pairs on opposite sides of the tube 6. Furthermore, the device 6 is provided with a neck portion 11, which may be provided with engagement means, such as flanges or threads 11'. In FIG. 3, a device 6 attached to a lid 12 of a cartridge is shown. Preferably, the neck portion 11 and the lid 12 are constructed so that the device 6 can be snapped onto the lid 12. Alternatively, the device 6 and the lid 12 can be made as an integral unit.

It is appreciated that the inventive device 6 as well as the cartridge 13 (vessel 14 and lid 12) (see e.g. FIG. 4) can be made of other materials than polypropylene.

Figure 4:
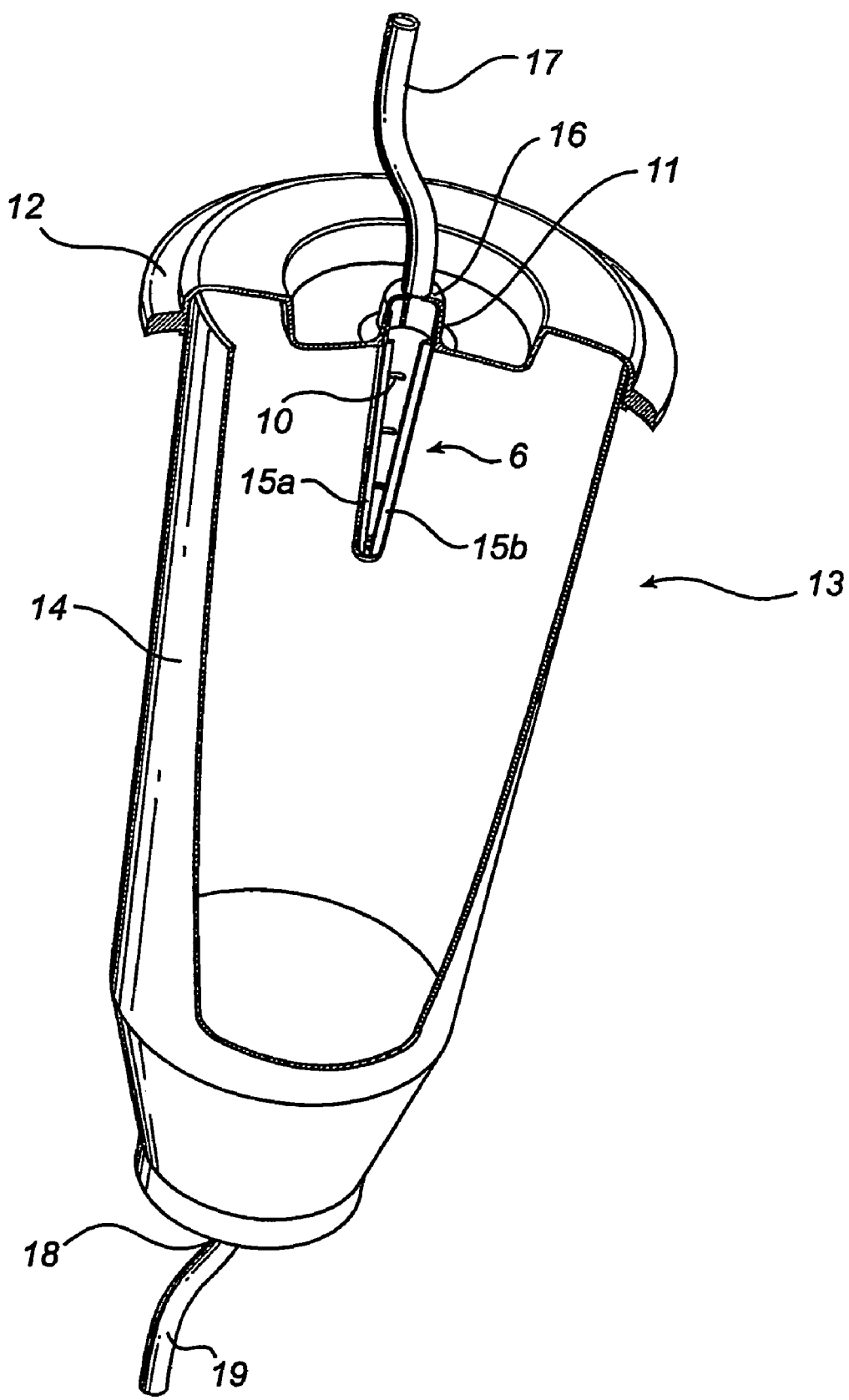
FIG. 4 is an isometric cut-away view of an inventive cartridge.

In FIG. 4, an embodiment of the inventive cartridge is shown. The cartridge 13 may be made of a polypropylene (or other material) vessel or container 14 and a polypropylene (or other material) lid 12. The lid 12 has a liquid permeable inlet 16. A solvent, which is to be introduced into the cartridge 13, may be supplied via a tube 17. In the bottom end of the vessel 14 a liquid permeable outlet 18 is provided. A tube 19 for discharge of a solution may be connected to the outlet 18. The tubes 17 and 19 may not necessarily form part of the inventive cartridge. Furthermore, the cartridge 13 has a conical tube 6 as disclosed above (cf. FIG. 2) connected at its neck portion 11 to the lid 12. The embodiment of the device 6 shown in FIG. 4 comprises two elongated flanges or ridges 15a, 15b. The ridges 15a, 15b are arranged longitudinally along and on the inside of the device 6. These ridges 15a, 15b may act as "fluid guides". The incoming fluid may then follow the inside wall of the tube 6 or flow along the ridges 15a, 15b. The "fluid guides" may alternatively consist of plastic pellets.

Figure 5:
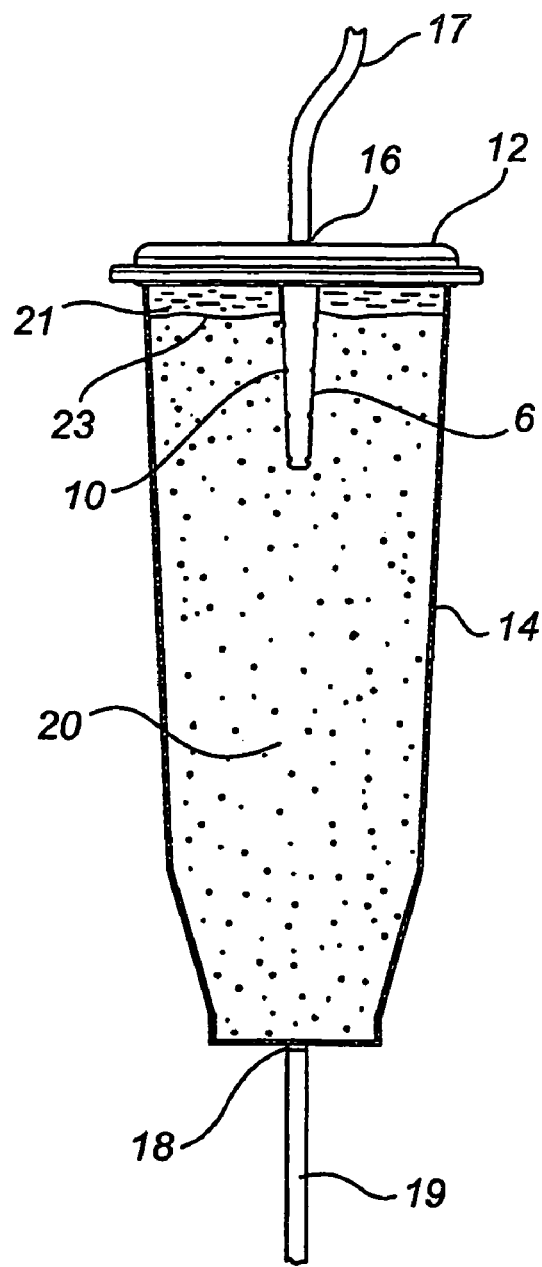
FIG. 5 and 6 illustrate the principle of the use of an inventive cartridge.

An inventive cartridge may be manufactured according to the following. Reference is made to FIGS. 4 and 5. A vessel 14 is provided and a batch of powder or granulate 20 is poured into the vessel 14. A tightly fitting lid 12 is attached to the vessel 14 so that the tube 6 is stuck into the powder bed 20. The lid 12 may be threaded or may be welded to the vessel 14. Alternatively, using a self-containing cartridge, the powder may be sucked into the vessel 14 through some kind of membrane.

In use (see FIGS. 5 and 6), first air is sucked from the cartridge 13 for the purpose of creating a vacuum in the cartridge. Then the cartridge is primed with a solvent, such as water, by letting solvent flow into the cartridge at a relatively high flow rate of about 1000 mL/min. It should be noted that the air removal and water priming may occur substantially simultaneously. In FIG. 5 a primed cartridge is shown. The solvent may be introduced either through the upper inlet 16 or the lower outlet 18, then having dual purpose, i.e. inlet at priming and outlet of saturated solution. In this example, the powder 20 may be sodium bicarbonate, and then the solvent 21 should be present in a sufficient amount so that the liquid level 22 is above the surface 23 of the powder bed 20. The powder 20 is dissolved in the solvent 21 and a saturated sodium bicarbonate solution may leave the cartridge 13 through the outlet 18. New solvent 21 is gradually entering the cartridge 13, at a relatively low flow rate which is less than or about the same as the rate of solution leaving the cartridge and may be of about 15 mL/min. The sodium bicarbonate solution may then be mixed outside the cartridge with a fluid containing electrolytes for yielding a dialysis fluid.

Figure 6:
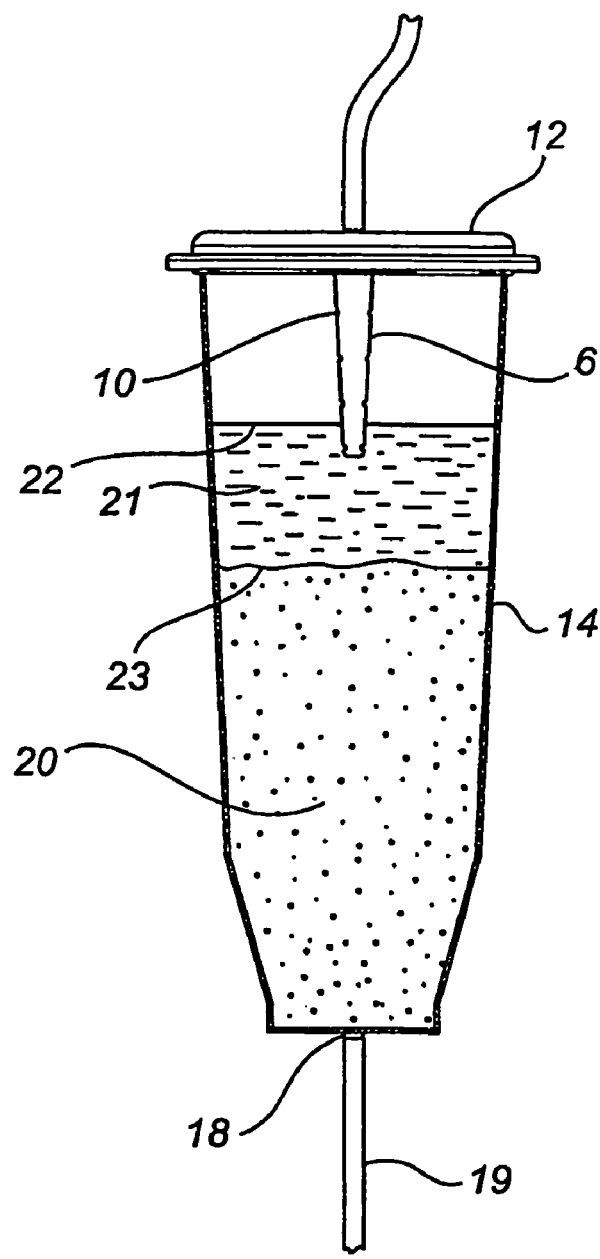

At least the lower holes of the tube 6 should be situated below the fluid level 22 and the fluid outlets 10 should be "directed" substantially towards the vessel wall so that the outflow of solvent 21 from the tube 6 is directed substantially horizontally, i.e. in parallel with the fluid level 22, as shown in FIG. 6.

The incoming fluid may then be prevented from freely falling in drops down to the fluid surface. The pressure waves and the currents will then be directed towards the wall of the vessel and dampened out before they reach the powder bed 20. The channeling effect is minimized. Tests have shown that the functioning time before an alarm is triggered can be prolonged as much as two hours compared to when using a prior-art cartridge intended for example for 8 h of use.

It should be noted that the cartridge 13 may also be formed without a lid, either as a closed vessel or an open vessel (not shown).

It is easily appreciated that the inventive device can be applied together with other types of cartridges, and the inventive idea for cartridges containing other substances than sodium bicarbonate. It is further appreciated that the inventive idea can be applied for other medical purposes than hemodialysis, such as for replacements fluids for hemodiafiltration and hemofiltration.

The invention claimed is:

1. A cartridge for on-line preparation of a solution, for a medical procedure, of water or other solvent and a solvable powder or granulate contained in the cartridge, comprising a vessel for containing said powder or granulate, said vessel being provided with at least one inlet for the solvent, and at least one outlet for the solution, said cartridge being provided with a device having a hollow body comprising:
    a first end which is open and connected to the inlet of the cartridge;
    a second end which is closed;
    a wall extending from the first end to the second end and being provided with through holes; and
    one or more ridges arranged longitudinally along an inside of the wall,
    wherein said first end is configured to receive a fluid introduced into the cartridge and to allow the fluid to exit the device through the through holes.

2. A cartridge according to claim 1, wherein said vessel contains a quantity of at least one concentrate in powder or granular form suitable for one treatment procedure.

3. A cartridge according to claim 1, wherein the cartridge has the form of a self-contained cartridge having fluid penetrable membranes at its inlet and outlet.

4. A method of employing of a cartridge according to claim 1 for on-line preparation of a solution for a medical procedure, the employment comprising the steps of:
    connecting the inlet of the cartridge to a source of water or other solvent, and
    connecting the outlet of the cartridge to a discharge means so that the solvent enters the cartridge via said device and so that the powder or granulate becomes dissolved in the solvent.

5. A cartridge according to claim 1, wherein the hollow body of the device has an elongated, tubular form.

6. A cartridge according to claim 1, wherein the hollow body of the device is in the form of a conical tube.

7. A cartridge according to claim 1, wherein the through holes are distributed along the hollow body of the device.

8. A cartridge according to claim 1, wherein the body at the first end has engaging means configured to connect the device to the cartridge.

9. A method for assembling a cartridge for on-line preparation of a solution for a medical procedure, of water or other solvent and a solvable powder or granulate contained in the cartridge, said method comprising the steps of:
    providing a vessel having an inlet for receiving said water or said other solvent from a source and having an outlet for delivering said solution,
    filling said vessel with a charge of said powder or granulate suitable for at least one treatment procedure, and
    arranging of a device on a downstream side of said inlet, said device having a hollow body comprising:
    a first end which is open and connected to the inlet of the cartridge;
    a second end which is closed;
    a wall extending from the first end to the second end and being provided with through holes; and
    one or more ridges arranged longitudinally alone an inside of the wall,
    wherein said first end is configured to receive a fluid introduced into the cartridge and to allow the fluid to exit the device through the through holes.

* * * * *

UNITED STATES PATENT AND TRADEMARK OFFICE
CERTIFICATE OF CORRECTION

PATENT NO.        : 7,632,474 B2                                          Page 1 of 1
APPLICATION NO.   : 10/552604
DATED             : December 15, 2009
INVENTOR(S)       : Losell It is certified that error appears in the above-identified patent and that said Letters Patent is hereby corrected as shown below:

Column 6, line 1, "employing of a" should read --employing a--.

Column 6, line 36, "alone" should read --along--.

Signed and Sealed this

Ninth Day of February, 2010

David J. Kappos
*Director of the United States Patent and Trademark Office*